(12) United States Patent
Wada et al.

(10) Patent No.: US 7,507,558 B2
(45) Date of Patent: *Mar. 24, 2009

(54) PROCESSES FOR PRODUCING INULIN

(75) Inventors: Tadashi Wada, Shizuoka (JP); Masao Ohguchi, Shizuoka (JP)

(73) Assignee: Fuji Nihon Seito Corporation, Tokyo (JP)

( * ) Notice: Subject to any disclaimer, the term of this patent is extended or adjusted under 35 U.S.C. 154(b) by 225 days.

This patent is subject to a terminal disclaimer.

(21) Appl. No.: 10/490,106

(22) PCT Filed: Sep. 26, 2002

(86) PCT No.: PCT/JP02/09958

§ 371 (c)(1),
(2), (4) Date: Mar. 25, 2004

(87) PCT Pub. No.: WO03/027304

PCT Pub. Date: Apr. 3, 2003

(65) Prior Publication Data

US 2004/0241810 A1 Dec. 2, 2004

(30) Foreign Application Priority Data

Sep. 26, 2001 (JP) .............................. 2001-293067

(51) Int. Cl.
C12P 19/04 (2006.01)
C12N 9/00 (2006.01)
C12N 9/10 (2006.01)
C12N 1/20 (2006.01)

(52) U.S. Cl. ...................... 435/101; 435/183; 435/193; 435/252.5

(58) Field of Classification Search ............... 435/252.5, 435/183, 193, 101
See application file for complete search history.

(56) References Cited

U.S. PATENT DOCUMENTS

| 5,478,732 A | 12/1995 | Kunz et al. |
| 5,952,205 A | 9/1999 | Catani et al. |
| 6,242,225 B1 * | 6/2001 | Catani et al. ................. 435/101 |
| 6,423,833 B1 | 7/2002 | Catani et al. |
| 6,500,805 B2 | 12/2002 | Van Loo et al. |
| 2003/0190711 A1 * | 10/2003 | Wada et al. ................. 435/101 |

FOREIGN PATENT DOCUMENTS

| WO | WO 99/57300 | 11/1999 |
| WO | 00/31287 | 6/2000 |
| WO | 02/00865 | 1/2002 |
| WO | EP 1298204 * | 4/2003 |

OTHER PUBLICATIONS

Kim et al. Selective production of GF4-fructooligosaccharide from sucrose by a new transfructosylating enzyme. 1998. Biotechnology Letters. 20(11):1031-1034.*

Elke M. Hellwege, et al., "Differences in chain length distribution of inulin from *cynara scolymus* and *helianthus tuberosus* are reflected in a transient plant expression system using the respective 1-FFT cDNAs", FEBS Letters, vol. 427, pp. 25-28 1998.

Elke M. Hellwege, et al., "Transgenic potato(*solanum tuberosum*) tubers synthesize the full spectrum of inulin molecules naturally occurring in globe artichoke (*cynara scolymus*)roots", Proc. Natl. Acad. Sci., vol. 97, No. 15, pp. 8699-8704 Jul. 18, 2000.

Jan Van Loo, et al., "On the presence of inulin and oligofructose as natural ingredients in the western diet", Critical Reviews in Food Science and Nutrition, vol. 35, No. 6, pp. 525-552.

Bacillus sp. 217C-11, published Mar. 5, 2001, vol. 75, p. 305 (Japanese reference and English translation).

* cited by examiner

*Primary Examiner*—L Blaine Lankford
*Assistant Examiner*—Taeyoon Kim
(74) *Attorney, Agent, or Firm*—Oblon, Spivak, McClelland, Maier & Neustadt, P.C.

(57) ABSTRACT

The present invention provides a method of producing inulin by bringing inulin synthase into contact with sucrose, wherein: (1) the average polymerization degree of inulin is regulated by controlling the sucrose concentration; (2) the average polymerization degree of inulin is regulated by controlling the temperature upon the above contact; and/or (3) at a stage when the above sucrose is consumed by the above inulin synthase and the reaction reaches an equilibrium state, sucrose is additionally added, and the reaction for generating inulin is further continued. Furthermore, the present invention relates to inulin having a predetermined average polymerization degree, which is obtained by the production method.

20 Claims, 6 Drawing Sheets

PROCESSES FOR PRODUCING INULIN

TECHNICAL FIELD

The present invention relates to a method of producing inulin by causing inulin synthase to act on sucrose, wherein the average polymerization degree of inulin is regulated by controlling the sucrose concentration, controlling the temperature at the time of reaction, and/or additionally adding sucrose. The present invention further relates to inulin having a predetermined average polymerization degree obtained by the production method.

BACKGROUND ART

Inulin is a type of polysaccharides, widely distributed in the natural world, and is known to be present in a colloidal form in the tubers of *Asteraceae* plants such as dahlias, Jerusalem artichokes, and wild chrysanthemums, and chicory roots. The characteristics of inulin are different from those of starch, such as the fact that inulin is dissolved in warm water and has a structure wherein D-fructofuranose is sequentially polymerized by dehydration onto the fructose side of sucrose via β-(2→1) linkages. The polymerization degree differs depending on the chain length of fructoses. In the case of inulin derived from a plant, the polymerization degree is in a range between about 8 to 60, and the average polymerization degree (average degree of polymerization) is described as being between 32 and 34 according to The Iwanami Dictionary of Biological Science (*Iwanami Seibutsugaku Jiten*, IWANAMI SHOTEN, 2nd edition (1978)) and being approximately 30 according to the Iwanami Dictionary of Physics and Chemistry (*Iwanami Rikagaku Jiten*, IWANAMI SHOTEN, 3rd edition (1979)).

Inulin has attracted attention as dietary fiber because it is water-soluble and is difficult to digest. Inulin further possesses an effect of promoting the growth of *Lactobacillus bifidus*, and thus its demand is growing in combination with the health-oriented boom in recent years. Inulin has been mainly produced abroad conventionally. Abroad, it is produced by cultivating plants such as chicory and Jerusalem artichoke and drying the juice extracted from the root stocks, and is utilized as a general food material. On the other hand, in Japan, commercial cultivation of these plants is difficult, so that inulin is not produced.

Hence, acquisition of inulin must depend on imports, and the price is more expensive than other domestic substances having a similar function, which is a barrier to industrial applications. Moreover, there are other problems in using inulin derived from a plant: the yield of inulin varies dependent on harvest conditions because its raw material is a plant; and, in the case where extraction is not performed immediately after harvesting, inulin content decreases due to self-digestion and the like.

Furthermore, in the case of inulin derived from a plant, since it is commercialized by roughly fractionating juice extracted from the plant and then spray-drying the product, the polymerization degree of inulin varies depending on the characteristics of the original plant. Therefore, the polymerization degree in the fructose chain ranges widely, and inulin having dispersed polymerization degrees (polymerization degree range: approximately 8 to 60) is obtained, resulting in lack of uniformity. For example, Critical Reviews in Food Science and Nutrition, 35(6), 525-552 (1995) discloses results showing the polymerization degrees of inulin from various plants (dahlia, chicory, and Jerusalem artichoke) obtained by HPAEC-PAD chromatography. A number of peaks were confirmed over a wide range in the polymerization degree between approximately 10 and 60 for inulins derived from plants, clearly suggesting their lack of uniformity. This problem would be solved by generating inulin showing a distribution of polymerization degree with high rate in a specific polymerization degree according to its use. However, this is very difficult.

In utilizing inulin, when an inulin fraction with an extremely high polymerization degree is used, its solubility in water is poor, resulting in an unfavorable situation upon actual application.

As a method of producing inulin in addition to the above extraction method from a plant, there exists a method of chemically producing inulin or inulin analogs utilizing inulin synthase. For example, M. Luscher et al (FEBS letter 385, 39 (1996)) reported a method of generating inulin from sucrose utilizing an enzyme obtained by extraction from a plant. This method use the coordinated action of 2 types of enzymes, sucrose: sucrose 1-fructosyltransferase (SST) and β-(2→1) fructan: β(2→1) fructan 1-fructosyltransferase (FFT). However, the preparation of these enzymes in large quantities from plant bodies requires time and effort, so that the use of this method on an industrial scale is not realistic.

Further, a method of producing an inulin analog, which causes the enzyme of a microbe to act, has been reported. For example, a method of obtaining a substance having an inulin-type structure, which involves treating conidiospores or cells of *Aspergillus sydowi* was disclosed (J. Biol. Chem., 43, 171(1920); Agric. Biol. Chem., 37, (9), 2111, (1973); JP Patent Publication (Kokai) No. 61-187797 A (1986); JP Patent Publication (Kokai) No. 5-308885 A (1993)). Furthermore, it was reported that an enzyme produced by microbes belonging to the genus *Aspergillus* or *Fusarium*, and another enzyme produced by microbes belonging to *Streptococcus mutans* generates an inulin analog, respectively (JP Patent Application No. 55-40193; Acta. Chem. Scand., B28, 589). The substances generated by the use of the enzymes produced by these microbes have structures analogous to that of inulin. However, compared with inulin derived from a plant, their molecules are quite large, or they differ in their binding forms, thus the above methods are not methods of generating inulin.

A method of generating inulin utilizing an enzyme derived from a microbe was disclosed in our co-pending patent application, PCT/JP01/01133. This is a method of producing inulin with relatively uniform polymerization degrees, which involves using sucrose as a raw material and causing a novel inulin synthase to act on it. With this method, the purpose of generating inulin utilizing an enzyme from a microbe has been achieved, and inulin with relatively uniform average polymerization degrees (average polymerization degree: 8 to 20) compared with inulin extracted from a plant could have been obtained. However, a means for effectively obtaining only inulin with a predetermined polymerization degree has not been established.

SUMMARY OF THE INVENTION

An object of the present invention is to provide a means to enable the production of inulin having a predetermined average polymerization degree in a method of producing inulin by causing inulin synthase to act on sucrose.

As a result of intensive studies to solve the above problem, we have found that, in reactions for producing inulin from sucrose using inulin synthase, the average polymerization degree of inulin can be regulated by controlling the sucrose concentration, controlling the temperature when inulin synthase is brought into contact with sucrose, and additionally adding sucrose during the reaction, to complete the present invention.

That is, the present invention provides the following (1) to (9).

(1) A method of producing inulin by bringing inulin synthase into contact with sucrose, wherein the average polymerization degree of inulin is regulated by controlling the sucrose concentration.
(2) A method of producing inulin by bringing inulin synthase into contact with sucrose, wherein the average polymerization degree of inulin is regulated by controlling the temperature upon contact.
(3) A method of producing inulin by bringing inulin synthase into contact with sucrose, wherein the average polymerization degree of inulin is increased by additionally adding sucrose at a stage when the above sucrose is consumed by the above inulin synthase and the reaction reaches an equilibrium state, and continuing reaction for generating inulin.
(4) The method of producing inulin of (3), wherein additional addition of sucrose is repeatedly conducted.
(5) The method of producing inulin of any one of (1) to (4), wherein the inulin synthase has action and substrate specificity such that it acts on sucrose to generate inulin, but does not act on kestose, maltose, lactose, trehalose and cellobiose.
(6) The method of producing inulin of any one of (1) to (5), wherein the inulin synthase is the culture solution or the cultured cells of a microbe producing the inulin synthase enzyme, or the treated product thereof.
(7) A method of producing inulin, comprising two or more methods selected from the method of (1), (2) and (3) being conducted in combination.
(8) A method of producing inulin having a predetermined average polymerization degree, wherein the method of any one of (1) to (7) is used.
(9) Inulin having a predetermined average polymerization degree, which is obtained using the method of any one of (1) to (7).

This specification includes part or all of the contents as disclosed in the specification and/or drawings of Japanese Patent Application No. 2001-293067, which is a priority document of the present application.

BEST MODE OF CARRYING OUT THE INVENTION

Figure 1:
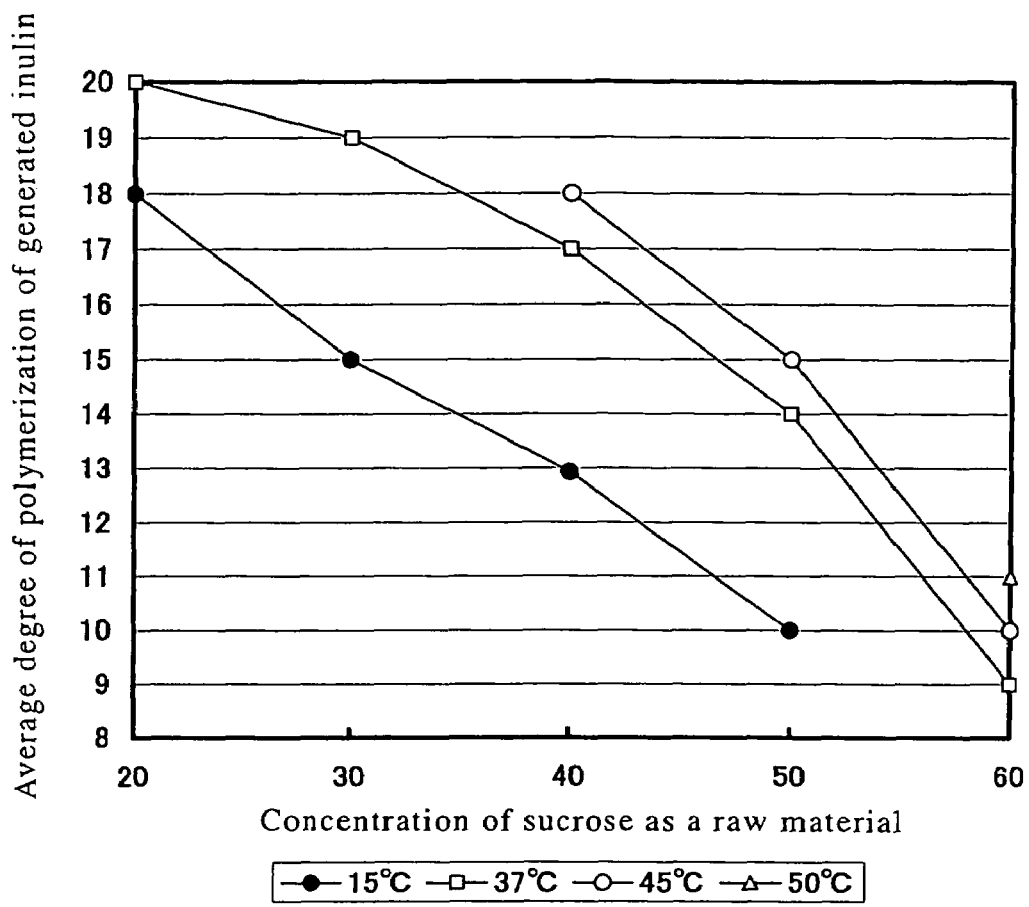
FIG. 1 shows the relationship between the sucrose concentration and the reaction temperature, and the average polymerization degree of inulin.

The method of producing inulin of the present invention will be further described below.

The method of the present invention includes various embodiments for regulating the average polymerization degree of inulin in a method of producing inulin by bringing inulin synthase into contact with sucrose to generate inulin.

In the present invention, "inulin" means a polysaccharide wherein D-fructofuranose is sequentially polymerized by dehydration onto the fructose side of sucrose via $\beta$-$(2\rightarrow1)$ linkage, and wherein 2 or more fructose molecules are polymerized to glucose. It also includes a fructo-oligosaccharide with a low polymerization degree wherein 2 to 4 fructose molecules are polymerized.

The expression "bringing inulin synthase into contact with sucrose" herein means that inulin synthase is added to a medium or the like containing sucrose as a carbon source, so as to allow them to react under conditions wherein they can generate inulin using sucrose as a substrate in the reaction solution.

Any enzyme may be used as an inulin synthase, as long as it has substrate specificity such that sucrose may be used for inulin synthesis. An example of the enzyme is an inulin synthase having action and substrate specificity such that it acts on sucrose to generate inulin but does not act on kestose, maltose, lactose, trehalose, and cellobiose.

Examples of the inulin synthase also include the culture solution or cultured cells of microbes producing the enzyme, or the treated product thereof. The "cultured cells" mean the above microbes cultured under appropriate conditions. They may be viable cells or lyophilized cells, and may also be in the form of acetone powder or the like. The "treated product" of cultured cells is not specifically limited, as long as the enzyme of the present invention can be collected without loss of its function. It includes, for example, the disrupted product of the above cultured cells, cell extracts, and immobilized cells. The disrupted product of cultured cells and the cell extracts mean substances and extracts obtained by disrupting the cells by a known disruption method, for example, an ultrasonication method, a Dynomill disruption method, or the French press disruption method. Furthermore, immobilized cells mean the above cells that are immobilized by a known immobilization method, for example, an entrapment method or a carrier binding method, and, if necessary, cross-linked. An example of the entrapment method is a method using natural polymers such as carrageenan or alginic acid.

Among the above inulin synthases, as the inulin synthase obtained from microbes producing an inulin synthase having action and substrate specificity such that it acts on sucrose to generate inulin but does not act on kestose, maltose, lactose, trehalose, and cellobiose, specifically, those obtained from the culture solution or cultured cells of *Bacillus* sp. 217C-11 strain (FERM BP-7450) described in PCT/JP01/01133, or the treated product thereof, can be used.

A method of culturing *Bacillus* sp. 217C-11 strain and preparing the enzyme will be briefly described below.

As a carbon source to be added to a medium, any carbon source that is generally used may be used at an appropriate concentration. For example, saccharides such as sucrose, glucose, fructose, or maltose may be used alone or in combination. When the enzyme, that generates inulin using sucrose as a substrate, is prepared with the strain, the most preferable carbon source is sucrose. By culturing the strain using a liquid medium containing sucrose as a main carbon source, the enzyme activity is improved. Of course, a sucrose-containing substance such as raw sugar or molasses may also be used.

As a nitrogen source, in addition to an organic nitrogen source such as peptone, meat extract, yeast extract, or corn steep liquor, an inorganic nitrogen source such as an ammonium salt of sulfuric acid, nitric acid or phosphoric acid can be used alone or in combination. As an inorganic salt, sulfate, hydrochloride, carbonate, nitrate, phosphate or the like of potassium, sodium, calcium, magnesium, manganese, iron or the like can be used alone or in combination. Furthermore, a source of nutrition or the like that is used for normal culture, such as amino acids or vitamins can optionally be used appropriately. As a medium appropriately used in the method of the present invention, a liquid medium with pH 7 to 8 containing 0.5% to 2% (w/v) sucrose, 1% peptone, 0.5% yeast extract and 0.2% dipotassium phosphate is preferably used.

Culture can be performed by shake-culture or using a jar fermentor under aerobic conditions. The pH of the medium preferably ranges from 6 to 9, the culture temperature preferably ranges from 25° C. to 37° C., and the time for culture may be at least a time during which microbes can proliferate, such as 5 to 96 hours, and preferably 15 to 72 hours.

*Bacillus* sp. 217C-11 strain can be cultured in the above described medium, microbes can be removed by centrifugation, and then the culture supernatant can be concentrated using an ultrafilter with a fractionation molecular weight of 30,000, so that the product can be used as an enzyme solution for reaction.

The inulin synthase, including an enzyme derived from *Bacillus* sp. 217C-11 strain, which has action and substrate specificity such that it acts on sucrose to generate inulin but does not act on kestose, maltose, lactose, trehalose, and cellobiose, possesses the following physicochemical properties.

Molecular weight: 45,000 to 50,000

Optimum temperature: 40 to 50° C.

Thermostability: begins to be gradually inactivated over 45° C., and shows 70% residual activity at 50° C. and 40% residual activity at 60° C.

Optimum pH: 7 to 8 (45° C.).

pH stability: stable at pH 6 or more

The concentration of the inulin synthase may be at a concentration where sucrose (substrate) in a reaction solution can be sufficiently utilized. For example, in the case of 40% to 60% (w/w) sucrose, a concentration at which the activity of the inulin synthase is 0.4 unit/ml reaction solution is preferred.

Regarding appropriate pH for the generation of inulin using sucrose as a substrate, a reaction solution with a pH range between 6 and 8 is preferably used. Furthermore, to maintain the pH of the reaction solution, a phosphate buffer can also be used. The reaction time can be appropriately changed depending on the amount of the inulin synthase used or other conditions, and generally ranges from 0.1 to 100 hours, and preferably from 0.5 to 72 hours.

The average polymerization degree of the thus obtained inulin can be analyzed as follows. The polymerization degree is based on the number of saccharide units (fructose and glucose units) in inulin. As an average polymerization degree, for example, the top of the peak in the analytical result obtained by a general analysis method such as HPLC, GC, or HPAEC can be employed. In this case, as a column, for example, ULTRON PS-80N (8×300 mm, manufactured by SHINWA CHEMICAL INDUSTRIES) (solvent: water, flow rate: 0.5 ml/min, temperature: 50° C.) or TSK-GEL G3000PWXL (7.8×300 mm, manufactured by TOSOH) (solvent: water, flow rate: 0.5 ml/min, temperature: 50° C.) may be used. The polymerization degree of the generated inulin can be confirmed with a differential refractometer as a detector, and determined using a calibration curve produced using as standard substances, for example, RAFITILINE ST (average polymerization degree=11) and RAFITILINE HP (average polymerization degree=22) of ORAFTI, which are inulins derived from plants. The analysis of the polymerization degree of inulin can also be carried out by referring to literature such as Critical Reviews in Food Science and Nutrition, 35(6), 525-552 (1995).

In the present invention, in the above method of producing inulin, the average polymerization degree of inulin to be generated can be regulated by (1) controlling the sucrose concentration, (2) controlling temperature upon contacting inulin synthase with sucrose, and (3) additionally adding sucrose.

Controlling sucrose concentration as the first means for regulating the average polymerization degree of inulin provides a method of producing inulin by bringing inulin synthase into contact with sucrose, wherein the average polymerization degree of inulin is regulated by controlling the sucrose concentration.

The sucrose concentration employed in the present invention is, for example, in the range between 3% and 68% (w/w), and preferably between 10% and 60% (w/w). By setting the sucrose concentration lower within the above range, the average polymerization degree of the resulting inulin can be higher. For example, when the reaction temperature is 15° C., whereas the average polymerization degree of inulin obtained with 50% sucrose concentration as a raw material is 10, the average polymerization degree of inulin obtained with 20% sucrose concentration as a raw material is 18. Moreover, when the reaction temperature is 37° C., whereas the average polymerization degree of inulin obtained with 60% sucrose concentration as a raw material is 9, the average polymerization degree of inulin obtained with 20% sucrose concentration as a raw material is 20. Therefore, appropriate setting of sucrose concentration can produce inulin with a desired average polymerization degree.

Controlling the temperature when inulin synthase is brought into contact with sucrose as the second means of regulating the average polymerization degree of inulin provides a method of producing inulin by bringing inulin synthase into contact with sucrose, wherein the average polymerization degree of inulin is regulated by controlling the temperature upon contact.

The reaction temperature when inulin synthase is brought into contact with sucrose ranges from 20 to 70° C., and preferably from 40 to 50° C. By setting the reaction temperature higher within the above range, the average polymerization degree of the resulting inulin becomes higher. For example, when the sucrose concentration is 50%, whereas the average polymerization degree of inulin is 10 at a reaction temperature of 15° C., that of inulin is 14 at a reaction temperature of 37° C. Furthermore, when the sucrose concentration is 30%, whereas the average polymerization degree of inulin is 15 at a reaction temperature of 15° C., that of inulin is 19 at a reaction temperature of 37° C. Therefore, appropriate setting of the reaction temperature can achieve a desired average polymerization degree of inulin.

Additional addition of sucrose as the third means of regulating the average polymerization degree of inulin provides a method of producing inulin by bringing inulin synthase into contact with sucrose, wherein at a stage when the initial sucrose is consumed by the above inulin synthase and the reaction reaches an equilibrium state, sucrose is additionally added, so as to continue the reaction for the generation of inulin.

The time for additionally adding sucrose is after the start of the production of inulin by bringing inulin synthase into contact with initially added sucrose, and is when the activity of inulin synthase is observed and the consumption of sucrose proceeds to some extent by the reaction. Such addition is particularly preferably conducted at a stage when the synthetic reaction reaches an equilibrium. The progress of the reaction can be confirmed by component analysis with HPLC.

The frequency of additional addition is not specifically limited, as long as the activity of inulin synthase remains and the synthetic reaction continues, and can be arbitrarily set depending on the desired average polymerization degree In order to obtain inulin with a high average polymerization degree, it is preferred to increase the frequency that sucrose is additionally added.

The above-described methods may be employed alone, or two or more methods may be employed in combination.

By performing the above method, inulin having a predetermined average polymerization degree can be obtained. The inulin having a predetermined average polymerization degree can be obtained by setting an optimum temperature, a temperature for contact, and/or additional addition of sucrose for obtaining inulin having any desired average polymerization degree between 8 and 25. Inulin having an average polymerization degree within the range of 8 to 12 can be obtained in a reaction by setting the sucrose concentration for 50% and the temperature for contact for 15° C., setting the sucrose concentration for 60% and the temperature for contact for 45° C., or setting the sucrose concentration for 60% and the temperature for contact for 50° C., for example. Inulin having an average polymerization degree within the range of 13 to 18 can be obtained by setting the sucrose concentration for 30% and the temperature for contact for 15° C., setting the sucrose concentration for 40% and the temperature for contact for 37° C., or setting the sucrose concentration for 50% and the temperature for contact for 45° C., for example. Furthermore, inulin having an average polymerization degree within the range of 19 to 25 can be obtained by setting the sucrose concentration for 20% and the temperature for contact for 37° C., or the sucrose concentration for 30% and the temperature for contact for 37° C., for example.

The thus obtained inulin of the present invention has a constant quality such that it shows less dispersion in the distribution of the polymerization degree in the fructose chain length, and a sharp distribution wherein a specific polymerization degree is at a high rate. The distribution in the polymerization degree in this specification refers to a dispersion range from the maximum value to the minimum value of the polymerization degree of the fructose chain length in inulin. The inulin of the present invention has the range of polymerization degree within ±20 from the average polymerization degree, and preferably within ±15 from the average polymerization degree. In terms of the range from the maximum value to the minimum value in the distribution of the polymerization degree, the polymerization degree of the inulin of the present invention has the range of 35 or less, and preferably 30 or less.

EXAMPLES

The present invention will be specifically described with examples, but these examples are not intended to limit the scope of the present invention.

Example 1

Preparation of Enzyme Solution from *Bacillus* sp. 217C-11 Strain

*Bacillus* sp.217C-11 strain (FERE BP-7450) was shake-cultured at 30° C. for 18 hours in a liquid medium with pH 7 to 8 containing 0.5% to 2% (w/v) sucrose, 1% peptone, 0.5% yeast extract, 0.2% dipotassium phosphate and 0.05% magnesium sulfate.

Next, solid ammonium sulfate was added to the culture supernatant, and then a fraction that had been precipitated with 70% saturation was collected using a centrifuge. The precipitate was then dissolved in 20 mM phosphate buffer with pH 7.0, and then put into a dialysis tube to sufficiently dialyze with the same buffer, thereby obtaining a crude enzyme solution. Subsequently, the crude enzyme solution was subjected to ion exchange chromatography and gel filtration chromatography using TSKgel DEAE TOYOPEARL 650 and TOYOPEARL HW55 manufactured by TOSOH and Sephacryl S-300 manufactured by Pharmacia according to a standard method, so that the inulin synthase of the present invention was purified. The enzyme was used as an enzyme preparation for reaction.

Example 2

Regulation of the Average Polymerization Degree of the Generated Inulin by Controlling the Sucrose Concentration and the Reaction Temperature The reaction solutions were prepared to contain the inulin synthase (2 u/ml) prepared in Example 1, 10 mM phosphate buffer (pH 7.0), and sucrose adjusted with water to have a final concentration of 20% (w/w), 30% (w/w), 40% (w/w), 50% (w/w), or 60% (w/w). The reaction solutions were placed in water baths with constant temperature set at 15° C., 37° C., 45° C., or 50° C., respectively, to conduct reactions for 48 hours. The results of the average polymerization degree of the generated inulin are shown in FIG. 1.

As a result, regardless of reaction temperature, the average polymerization degree of the generated inulin became higher as the sucrose concentration in the reaction solution became lower. In addition, in cases with the same sucrose concentration, it was confirmed that the average polymerization degree of the generated inulin increased as the reaction temperature was higher.

Example 3

Regulation of the Average Polymerization Degree of Inulin by Additional Addition of Sucrose 100 g of a reaction solution prepared by adding water to 40 g of sucrose and 2.4 to 4 g of 30 u/ml inulin synthase prepared in Example 1 was put into a 500 ml Erlenmeyer flask, so that a reaction was performed while agitating the solution at 150 rpm (hereinafter, referred to as the 1st reaction). At the time when the consumption of sucrose had almost stopped, 40% (w/w) sucrose was added to the 1st reaction solution while varying the amount of sucrose from 20 g to 100 g, and again, the reaction was continued until the consumption of sucrose stopped (hereinafter referred to as the 2nd reaction). In addition, since inulin synthase is diluted by additional addition of sucrose, to make all the final concentrations of the added enzyme constant, the amount of the enzyme added at the stage of the 1st reaction was varied for adjustment.

Figure 2:
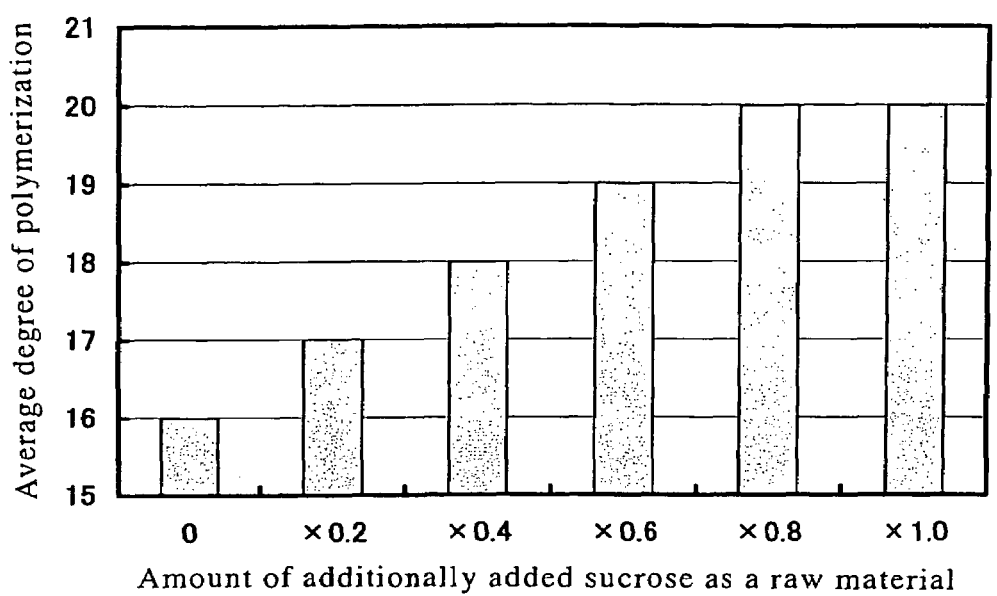
FIG. 2 shows the relationship between the additional addition of sucrose and the average polymerization degree of inulin.

Table 1 shows the amount of inulin synthase added, the reaction times, the values obtained by the component analysis of the reaction solution, and the average polymerization degrees of the generated inulin in the 1st reaction. Table 2 shows the amount of sucrose additionally added, the reaction times, the values obtained by the component analysis of the reaction solution, and the average polymerization degrees of the generated inulin in the 2nd reaction. FIG. 2 shows differences in the average polymerization degrees of the generated inulin due to the differences in the amount of sucrose additionally added. As a result, it was confirmed that the higher the amount of sucrose additionally added after the 1st reaction, the higher the average polymerization degree of the generated inulin.

TABLE 1

Results of the 1st reaction
1st reaction

| Amount of enzyme (g) | Time (hr) | HPLC (sugar composition %) | | | | DP(*) |
|---|---|---|---|---|---|---|
| | | inulin | sucrose | glucose | fructose | |
| 2.4 | 22 | 44.8 | 7.7 | 44.1 | 2.3 | 16 |
| 2.8 | 20 | 44.8 | 7.6 | 44.2 | 2.3 | 16 |
| 3.2 | 18 | 44.8 | 7.5 | 44.3 | 2.3 | 16 |
| 3.6 | 16 | 44.7 | 7.5 | 44.3 | 2.3 | 16 |
| 4.0 | 14 | 44.7 | 7.5 | 44.3 | 2.3 | 16 |

DP = average polymerization degree

TABLE 2

Results of the 2nd reaction
2nd reaction

| Additional addition Sucrose (g) | Time (hr) | HPLC (sugar composition%) | | | | DP(*) |
|---|---|---|---|---|---|---|
| | | inulin | sucrose | glucose | fructose | |
| 20 | 16 | 44.4 | 8.5 | 44.0 | 2.4 | 17 |
| 40 | 18 | 44.0 | 9.1 | 43.9 | 2.3 | 18 |
| 60 | 20 | 43.6 | 9.5 | 43.9 | 2.3 | 19 |
| 80 | 22 | 43.2 | 10.3 | 43.5 | 2.3 | 20 |
| 100 | 24 | 43.5 | 9.6 | 43.9 | 2.4 | 20 |

DP = average polymerization degree

Example 4

Figure 3:
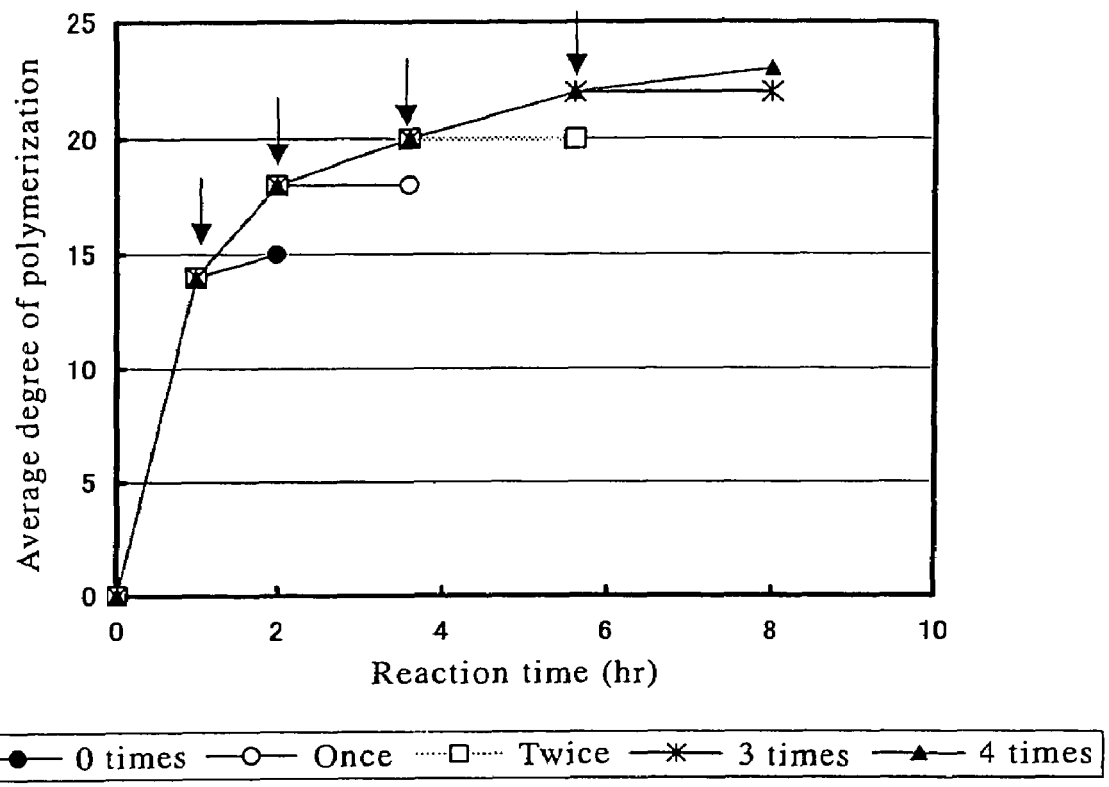
FIG. 3 shows the relationship between frequency of additional addition of sucrose and the average polymerization degree of inulin. Arrows denote the time of additional addition.

Regulation of the Average Polymerization Degree of the Generated Inulin by Controlling Frequency of Additional Addition of Sucrose The 1st reaction was performed at 60° C. using a solution prepared by adding 0.25 ml of 0.4 M phosphate buffer (pH 7) and 4 g of 30 u/ml inulin synthase to 5 g of sucrose and adjusting the weight of the solution to 10 g with water. At the stage where the consumption of sucrose in the 1st reaction reached an equilibrium state, each 5 g of 50% (w/w) sucrose solution (pH 7) was additionally added per addition, so that the 2nd reaction was continued. This procedure was repeated 4 times, and then the average polymerization degree of inulin generated at each time was examined. FIG. 3 shows the results. As is clear from FIG. 3, as frequency of additional addition of sucrose increased, the polymerization degree of inulin increased. The average polymerization degree of inulin obtained via 4 times additional addition reached 23.

Example 5

Examination of the Distribution of the Polymerization Degree

Figure 4:
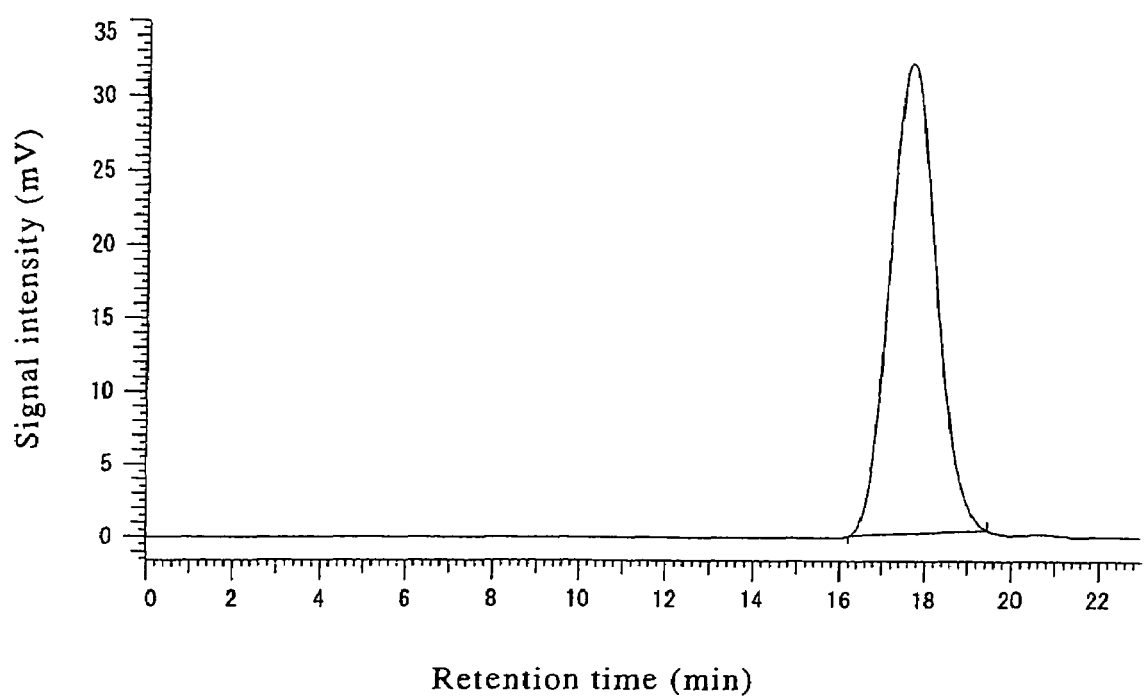
FIG. 4 shows the result of HPLC analysis for the inulin (average polymerization degree=17) of the present invention.
Figure 5:
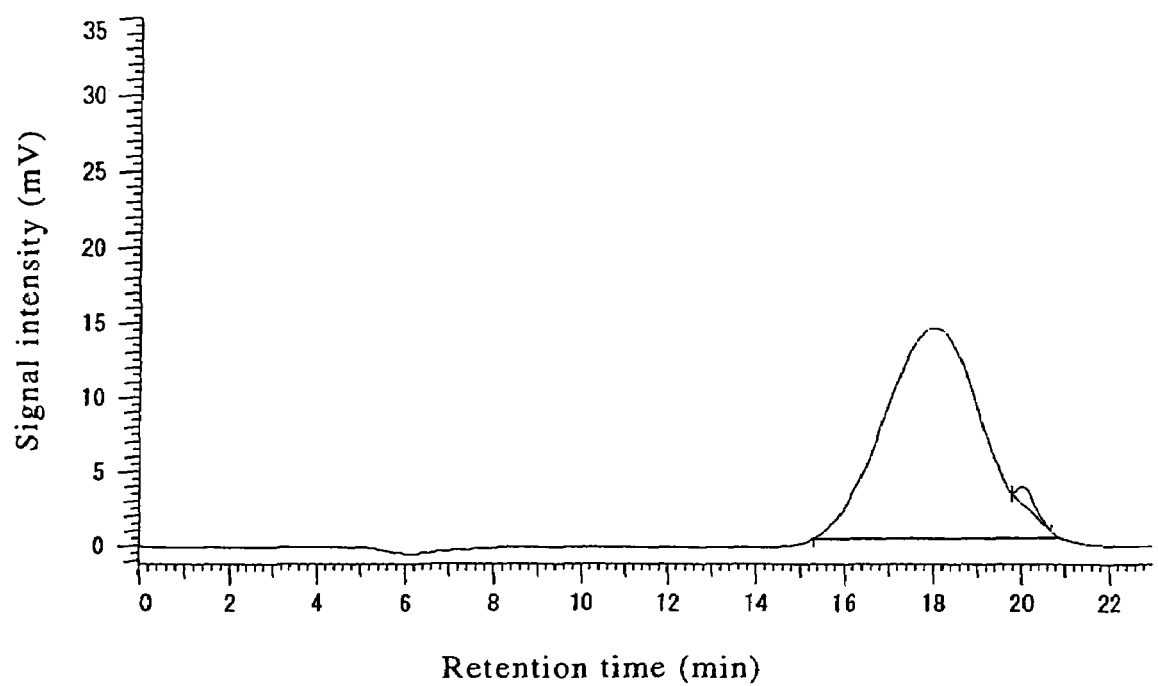
FIG. 5 shows the result of HPLC analysis for RAFTILINE ST (average polymerization degree=11, ORAFTI) derived from a plant.
Figure 6:
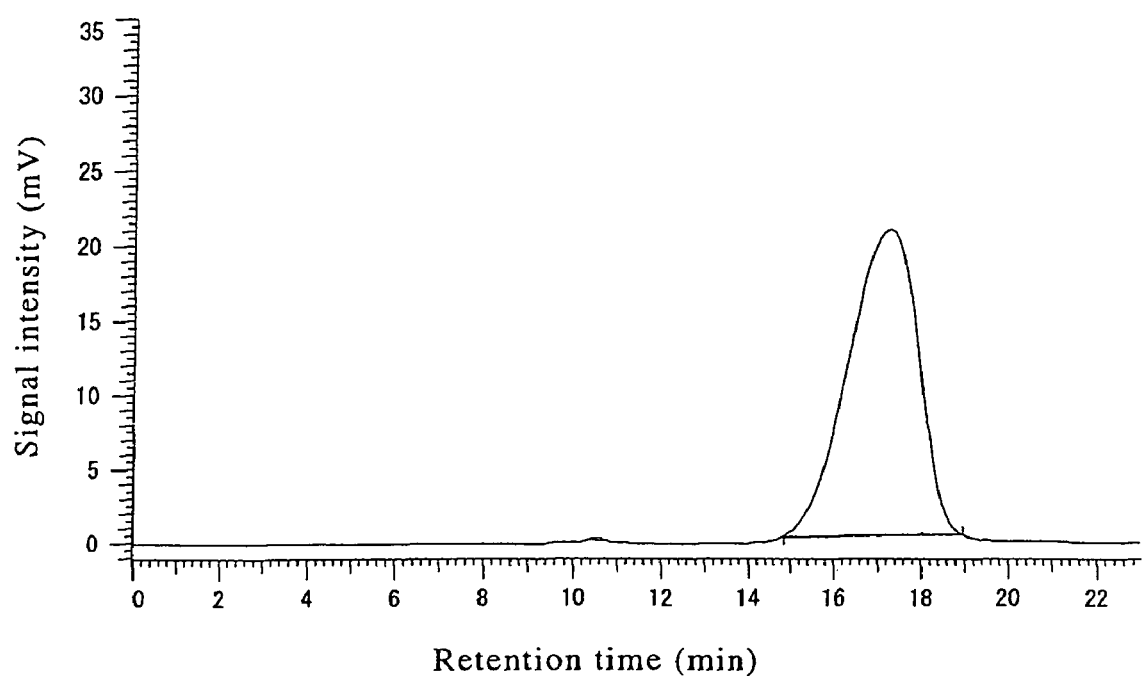
FIG. 6 shows the result of HPLC analysis for RAFTILINE HP (average polymerization degree=22, ORAFTI) derived from a plant.

The polymerization degree of the inulin of the present invention, that had been confirmed by HPLC analysis using TSK-GEL G3000PWXL manufactured by TOSOH (7.8×300 mm) as a column (solvent: water, flow rate: 0.5 ml/min, temperature: 50° C.) and a differential refractometer as a detector, was determined with a calibration curve that had been produced using as standard substances RAFTILINE ST (average polymerization degree=11) and RAFTILINE HP (average polymerization degree=22) of ORAFTI, which are inulins derived from plants. The distributions of the polymerization degree were compared among the inulin of the present invention and the inulins derived from the plants. FIG. 4 shows the result for the inulin of the present invention, and FIGS. 5 and 6 show the results for RAFTILINE ST (average polymerization degree of 11) and RAFTILINE HP (average polymerization degree of 22), respectively. As is clear from these results, the inulin of the present invention (average polymerization degree of 17) showed a peak which is narrower and higher than those of the inulins derived from the plants used as standard substances.

The specific range of the distribution in the polymerization degree was determined for the inulin of the present invention and RAFTILINE HP, the inulin derived from a plant. In the case of the inulin of the present invention, whose average polymerization degree was 17, the distribution in the polymerization degree ranged from 4 to 30. On the other hand, in the case of RAFTILINE HP, whose average polymerization degree was 22, the distribution in polymerization degree ranged from approximately 8 to 60, revealing that the dispersion range in the chain length of the inulin of the present invention was approximately half of that of RAFTILINE HP.

Accordingly, since the inulin of the present invention has small dispersion in the polymerization degree, and shows a distribution with high rate in specific polymerization degree, it is clear that the inulin has very constant quality.

INDUSTRIAL APPLICABILITY

According to the present invention, in the method of producing inulin by bringing inulin synthase into contact with sucrose to generate inulin, inulin having a specific average polymerization degree can be artificially produced by controlling reaction conditions including the sucrose concentration and/or the reaction temperature, or performing once or more the additional addition of sucrose. As a result, it becomes possible to collect only an inulin fraction having a desired and most effective average polymerization degree according to a specific situation, so that obtained inulin can be further effectively utilized according to its use.

All publications, patents, and patent applications cited herein are incorporated herein by reference in their entirety.

The invention claimed is:

1. A method of producing inulin having an average degree of polymerization ranging from 8 to 25 comprising:
   contacting inulin synthase from *Bacillus* sp. 217C-11 (FERM BP-7450) with sucrose,
   wherein the average polymerization degree of inulin is regulated by controlling the sucrose concentration.

2. The method of claim 1, further comprising regulating the average polymerization degree of inulin by controlling the temperature during said contacting.

3. The method of claim 1, wherein the average polymerization degree of inulin is increased by adding more sucrose at a stage when an initial amount of sucrose is consumed by the inulin synthase and the reaction reaches an equilibrium state, and continuing the reaction for generating inulin.

4. The method of claim 3, further comprising multiple additions of more sucrose.

5. The method of producing inulin of claim 1, wherein the inulin synthase is comprised in a culture solution, in cultured cells of *Bacillus* sp. 217C-11 (FERM BP-7450) producing the inulin synthase, in a disrupted product of the cultured cells, in a cell extract, or in immobilized cells.

6. The method of claim 1, which produces inulin having a range of polymerization degree of 2 to 30 in terms of the range from the maximum value to the minimum value in the distribution of the polymerization degree.

7. The method of claim 1, further comprising regulating the average polymerization degree of inulin by adding sucrose.

8. The method of claim 1, wherein the average degree of polymerization for the inulin is increased by adding sucrose at the stage when sucrose is consumed by the inulin synthase.

9. The method of claim 7, wherein the average degree of polymerization for the inulin is increased by adding sucrose at the stage when sucrose is consumed by the inulin synthase.

10. The method of claim 1 comprising:
    contacting inulin synthase from *Bacillus* sp. 217C-11 (FERM BP-7450) with sucrose under conditions suitable for the production of inulin, and
    recovering inulin having an average degree of polymerization ranging between 8 and 25;
    wherein said inulin synthase acts on sucrose to produce inulin, but does not act on kestose, maltose, lactose, tehalose or cellobiose; and
    wherein said inulin synthase has a molecular weight ranging from 45,000 Da to 50,000 Da.

11. The method of claim 10, wherein said inulin has an average degree of polymerization ranging from 8 to 12.

12. The method of claim 10, wherein said inulin has an average degree of polymerization ranging from 13 to 18.

13. The method of claim 10, wherein said inulin has an average degree of polymerization ranging from 19 to 25.

14. The method of claim 10, further comprising selecting a sucrose concentration between 3% and 68% that produces a predetermined average degree of polymerization of the inulin.

15. The method of claim 10, further comprising selecting a reaction temperature between 20° C. and 70° C. that produces a predetermined average degree of polymerization of the inulin.

16. The method of claim 10, further comprising adding more sucrose, after initially contacting inulin synthase and an initial amount of sucrose, in an amount suitable to produce inulin having a predetermined average degree of polymerization.

17. The method of claim 1, which is conducted at an initial sucrose concentration between 10% and 60% and at a temperature between 40° C. and 50° C.

18. The method of claim 10, wherein said inulin synthase has the following physiochemical properties:
    optimum temperature: optimum activity at 40° C. to 50° C.,
    thermostability: the inulin synthase begins to be gradually inactivated at a temperature over 45° C., and shows at least 70% residual activity at 50° C. and at least 40% residual activity at 60° C.,
    optimum pH: has optimum activity at pH 7 to 8, and
    pH stability: is stable at pH 6 or higher.

19. The method of claim 10, wherein the inulin synthase is isolated from *Bacillus* sp. 217C-11 (FERM BP-7450).

20. A method of producing inulin having an average degree of polymerization ranging from 8 to 25 comprising:
    contacting inulin synthase from *Bacillus* sp. 217C-11 (FERM BP-7450) with sucrose;
    wherein the average degree of polymerization is regulated by controlling the sucrose concentration, the temperature at the time of reaction, and/or by adding additional sucrose during the reaction.

* * * * *